United States Patent [19] [11] 4,223,012
Anderson et al. [45] Sep. 16, 1980

[54] METHOD FOR CONTROL OF SAN JOSE SCALE

[75] Inventors: Richard J. Anderson; Clive A. Henrick, both of Palo Alto, Calif.

[73] Assignee: Zoecon Corporation, Palo Alto, Calif.

[21] Appl. No.: 26,156

[22] Filed: Apr. 2, 1979

[51] Int. Cl.² ............................................. A01N 17/14
[52] U.S. Cl. ................................. 424/84; 260/410.9 R; 560/249; 568/875
[58] Field of Search ....................... 560/205, 261, 249; 562/598; 424/84; 568/875

[56] References Cited

U.S. PATENT DOCUMENTS

| | | | |
|---|---|---|---|
| 2,677,701 | 5/1954 | Surmatis et al. | 560/261 |
| 4,010,255 | 3/1977 | Carde et al. | 424/84 |
| 4,034,080 | 7/1977 | Silverstein et al. | 424/84 |
| 4,107,293 | 8/1978 | Swailes et al. | 424/84 |

*Primary Examiner*—Natalie Trousof
*Assistant Examiner*—L. Hendriksen

[57] ABSTRACT

An attractant, and synthesis thereof, for the San Jose scale, *Quadraspidiotus perniciosus*.

3 Claims, No Drawings

METHOD FOR CONTROL OF SAN JOSE SCALE

This invention relates to an attractant, and synthesis thereof, for the San Jose scale, *Quadraspidiotus perniciosus* (Comstock). The San Jose scale is a pest of fruit.

In our prior application Ser. No. 956,292, filed Oct. 30, 1978, we reported the synthesis of a component of the natural sex pheromone, the cis isomer of 3,7-dimethyl-2,7-octadien-1-yl propionate, for attracting the male San Jose scale. We have discovered that the trans isomer, that is, (E)-3,7-dimethyl-2,7-octadien-1-yl propionate, is a potent attractant for the male San Jose scale. The attractancy of (E)-3,7-dimethyl-2,7-octadien-1-yl propionate for the male San Jose scale is superior to the attractancy of the natural cis isomer.

The attractant of the present invention is useful in conjunction with traps to monitor populations of, or to mass trap, the San Jose scale. The amount of attractant needed for each trap is very small. Generally, an amount from about 25 to 500 micrograms per trap is effective. The attractant may be conveniently dispensed by, for example, diluting the attractant in hexane and placing the calculated amount in a rubber septa which is then placed in a trap having a sticky adhesive coating. The attractant is useful also in the confusion or mating disruption technique of insect control which involves releasing an amount of the compound sufficient to permeate the air over an area desired to be protected. By this technique the San Jose scale is unable to orientate properly and thereby mating is disrupted. The attractant may also be blended with a plastic such as polyvinyl chloride or placed in micro-dispensers for ease of handling and dispensing. Suitable traps and carriers are described in U.S. Pat. No. 3,866,349 and 4,010,255.

The following examples are provided to illustrate the practice of the present invention. Temperature is given in degrees Centigrade.

EXAMPLE 1

To a mixture of rinsed lithium pieces (23 mmol), under argon, and 5 ml of dry ether is added 1-bromo-4-methyl-4-pentene (11.5 mmol) over about 40 minutes, while cooling in an ice bath. After addition is completed, the reaction mixture is stirred for about 3 hours.

The above prepared lithium reagent (6.4 mmol) is added to a mixture of cuprous iodide (6.01 mmol) and ether (15 ml), under argon, and at $-40°$ to $-50°$. Tetramethylethylenediamine (7.7 mmol) is added and then after about 35 minutes methyl 2-butynoate (5.8 mmol) in one ml of ether is added. After 60 minutes at $-45°$, 2 ml of methanol is added dropwise, followed by 2 ml of saturated aqueous ammonium sulfate. The reaction mixture is stirred for about 16 hours and then worked up by filtering through celite and rinsing with about 100 ml of ether. The combined ether phases are washed with ammonium sulfate solution, dilute HCl and brine, dried over magnesium sulfate and solvent removed under vacuum. The product is thin layer chromatographed on 1 meter plates using 4% ether/hexane and then 3% ether/hexane and the major band is collected to give methyl (E)-3,7-dimethyl-2,7-octadienoate.

To a mixture of the foregoing dienoic ester (0.827 mmol) and 7.5 ml of benzene, under nitrogen, is added 1.5 ml of 1.78 M diisobutyl aluminum hydride (DIBAH). After about 2 hours, 1 ml more of DIBAH is added and the reaction continued to completion as checked by thin layer chromatography. The reaction is worked up by adding about 2 ml of methanol and dilute HCl. The aqueous layer is extracted with ether. Then the combined ether phases are washed with water and brine, dried over sodium sulfate and solvent evaporated to yield (E)-3,7-dimethyl-2,7-octadien-1-ol.

A mixture of the foregoing diene alcohol (0.785 mmol), propionic anhydride (1.5 mmol) and pyridine (0.15 ml) is heated, under nitrogen, to 85° for about 2 hours. The reaction is worked up using dilute HCl and ether. The combined ether phases are washed with dilute HCl, aqueous sodium bicarbonate and brine, dried over magnesium sulfate and the solvent is removed under vacuum. The product is purified by thin layer chromatography using 5% ether/hexane and then is microdistilled (bath, 0.01 mm, 45°–50°) to yield (E)-3,7-dimethyl-2,7-octadien-1-yl propionate.

EXAMPLE 2

Rubber septa caps (5) are charged with 33 micrograms of (A) (E)-3,7-dimethyl-2,7-octadien-1-yl propionate diluted in hexane, (B) (Z)-3,7-dimethyl-2,7-octadien-1-yl propionate diluted in hexane and (C) hexane only as control. Each rubber septa was placed in a trap and the catch of male San Jose scale recorded as follows:

|  | Catch of Male San Jose Scale | | | | |
| --- | --- | --- | --- | --- | --- |
|  | I | II | III | IV | V |
| (A) (E)-3,7-dimethyl-2,7-octadien-1-yl propionate | 58 | 43 | 139 | 162 | 42 |
| (B) (Z)-3,7-dimethyl-2,7-octadien-1-yl propionate | 31 | 28 | 70 | 95 | 12 |
| (C) Hexane control | 3 | 4 | 6 | 11 | 2 |

The attractant (A) of the present invention surpassed the catch of the cis isomer (B) in each trial (I-V) considerably.

What is claimed is:

1. In a method for the control of San Jose scale, *Quadraspidiotus perniciosus*, by subjecting said scale to an attractant in an amount sufficient to attract the scale to a particular location, the improvement which comprises the use as said attractant of an effective amount of (E)-3,7-dimethyl-2,7-octadein-1-yl propionate.

2. The method of claim 1 wherein said attractant is placed in an insect trap.

3. The method of claim 1 wherein said attractant is used to permeate the air over an area which it is desired to protect from said scale.

* * * * *